(12) United States Patent
Davis

(10) Patent No.: US 7,660,617 B2
(45) Date of Patent: Feb. 9, 2010

(54) ELECTRICAL IMPEDANCE TOMOGRAPHY USING A VIRTUAL SHORT MEASUREMENT TECHNIQUE

(75) Inventor: Grant E. Davis, Mercer Island, WA (US)

(73) Assignee: The Boeing Company, Chiacgo, IL (US)

( * ) Notice: Subject to any disclaimer, the term of this patent is extended or adjusted under 35 U.S.C. 154(b) by 685 days.

(21) Appl. No.: 11/271,776

(22) Filed: Nov. 10, 2005

(65) Prior Publication Data

US 2006/0116599 A1  Jun. 1, 2006

Related U.S. Application Data

(60) Provisional application No. 60/627,549, filed on Nov. 12, 2004.

(51) Int. Cl.
*A61B 5/05* (2006.01)
(52) U.S. Cl. .................................. 600/407; 600/547
(58) Field of Classification Search ................ 600/547, 600/407, 393, 461, 476, 477, 478; 324/600, 324/603, 605, 609, 629, 601, 611
See application file for complete search history.

(56) References Cited

U.S. PATENT DOCUMENTS 6,560,480 B1 * 5/2003 Nachaliel et al. ............ 600/547

OTHER PUBLICATIONS

G.J. Saulnier et al, Electrical Impedance Tomography, IEEE Signal Processing Magazine, Nov. 2001, pp. 31-43.
Configuring a Register Network Test System with the Model 2400 SourceMeter Instrument, Keithley Instruments, Inc., 2001.
Thomas Schwertner, Obtaining More Accurate Resistance Measurements Using the 6-wire Ohms Measurement Technique, Keithley Instruments, Inc., 2000.

* cited by examiner

*Primary Examiner*—Brian Casler
*Assistant Examiner*—Elmer Chao
(74) *Attorney, Agent, or Firm*—Yee & Associates, P.C.; Brook Assefa

(57) ABSTRACT

Typical electrical impedance tomography ("EIT") systems apply current to a body under test and measure the induced voltages on the surface and then through an inverse process, reconstruct an approximation to the electrical conductivity in the interior. The EIT system described herein employs a new approach to evaluating the interior electrical conductivity by using a virtual short that allows both current and voltages to be measured at various locations on the body under test. The architecture of this system is described, distinguishability of embedded conductive anomalies is evaluated, typical error sources associated with a virtual short measurement is discussed in the context of electrical impedance tomography, and a new imaging system is discussed.

14 Claims, 10 Drawing Sheets

ELECTRICAL IMPEDANCE TOMOGRAPHY USING A VIRTUAL SHORT MEASUREMENT TECHNIQUE

CROSS-REFERENCE TO RELATED APPLICATION

This application claims the benefit of U.S. provisional patent application Ser. No. 60/627,549, filed Nov. 12, 2004.

TECHNICAL FIELD

The present invention relates to sensor systems and sensing methods, particularly to electrical impedance tomography.

BACKGROUND

Electrical impedance tomography ("EIT") is an imaging modality that evaluates the conductivity within the interior of objects using resistance measurements obtained from electrodes/sensors on that object's outer surface. In the typical measurement, currents are injected into the object through electrodes placed on the surface of the object, with voltages measured at other electrodes. Considerable effort has been invested in determining current distributions that will provide best clarity in viewing and conductivity profile within the object. Input currents are defined at each electrode, voltages are measured at each electrode, and then the conductivity profile of the object is reconstructed. This reconstruction process is an inverse problem that is considerably more difficult than many other imaging modalities such as x-ray computed tomography because the current paths in an EIT measurement are able to greatly adjust themselves to an object's interior conductive profile. Another problem with conventional EIT measurement is that large changes at localized sections in the object's interior will produce only small changes in measured voltages at the exterior. In this regard, a challenging task for EIT is to reconstruct the internal impedance profile given low level, noisy voltage measurements. Conventional aspects of EIT are discussed in "Electrical Impedance Tomography," IEEE Signal Processing Magazine, November 2001, which is incorporated by reference herein.

Systems such as adaptive current tomography ("ACT") have been developed to provide an impedance image for a body. In ACT, electrodes are placed on the exterior of a body and currents are then applied simultaneously to each electrode. Electrode voltages are then measured to generate the data required to perform an image reconstruction. These electrodes may be placed in a single plane or in several layers. A third generation ACT system (which is denoted as ACT3) uses 32 electrodes, and the applied currents are 28.8 kHz sinusoids, resulting in a system that can measure both lossy and reactive components of the impedance. This ACT instrument is real-time and is capable of producing about 20 images per second. The ACT3 system has some shortcomings. For example, it is difficult to: (1) accurately discern impedance anomalies in the interior of an object; (2) accurately evaluate the impedance values of these anomalies; and (3) spatially resolve the anomaly in an accurate manner.

Numerous algorithms have been proposed to use electrical measurements derived from EIT to reconstruct an object's conductivity profile. A typical approach for determining the conductivity profile within an object is to model the object as a resistive network. The discrete resistors within this network are treated as unknowns. The resistance value of each of the discrete resistors is determined by minimizing the least squares error in the voltage measurements at each electrode.

The measure or degree with which a measurement system can detect an impedance anomaly is referred to as distinguishability. Measurement systems with greater distinguishability should generally provide improved image data for an observed body. Generally an algorithm or measurement process that has more distinguishability will provide more superior conductive profile reconstruction. Thus, high distinguishability is a desirable trait in EIT systems.

Accordingly, it is desirable to have an EIT system that addresses the above shortcomings of conventional measurement techniques. Furthermore, other desirable features and characteristics of the present invention will become apparent from the subsequent detailed description and the appended claims, taken in conjunction with the accompanying drawings and the foregoing technical field and background.

BRIEF SUMMARY

An EIT system and method according to the present invention channels an electrical current to a greater extent than past approaches in EIT. The technique described herein uses virtual shorts to evaluate the conductivity profile within a measured object. The measurement technique also uses virtual shorts to evaluate the resistance through a section of an object. The resistance through a section of the object is evaluated by measuring the voltage across the section of the object divided by the current flowing through that section of the body. The voltage and current measurements through that section of the body both have better resolution and greater distinguishability than earlier measurement approaches to EIT. Improved resolution and greater distinguishability should also provide an improved imaging capability.

The above and other aspects of the invention may be carried out in one form by an EIT method for evaluating interior features of a body under test with a plurality of electrodes. The method involves: designating a first one of the plurality of electrodes as a source electrode, and a second one of the plurality of electrodes as a sink electrode; establishing a virtual short between the source electrode and at least one of the plurality of electrodes other than the sink electrode; applying a test current to the source electrode; and measuring a sense voltage between the source electrode and the sink electrode.

BRIEF DESCRIPTION OF THE DRAWINGS

A more complete understanding of the present invention may be derived by referring to the detailed description and claims when considered in conjunction with the following figures, wherein like reference numbers refer to similar elements throughout the figures.

DETAILED DESCRIPTION

Figure 1:
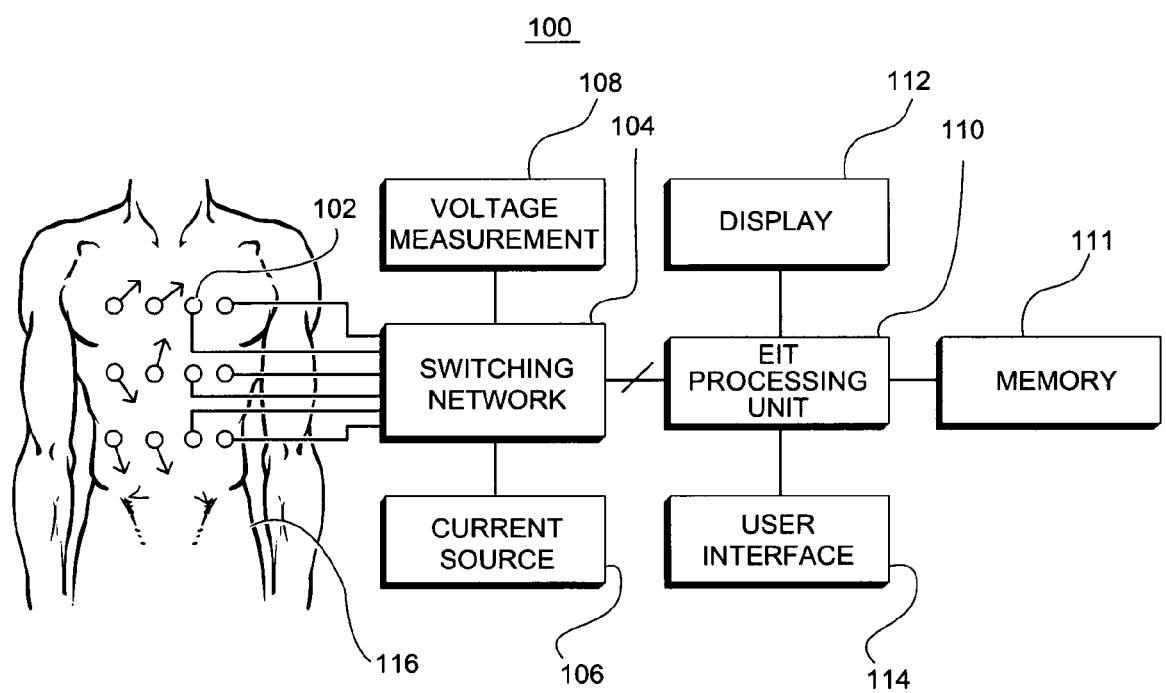
FIG. 1 is a schematic representation of an EIT system configured in accordance with an example embodiment of the invention.

The following detailed description is merely illustrative in nature and is not intended to limit the invention or the application and uses of the invention. Furthermore, there is no intention to be bound by any expressed or implied theory presented in the preceding technical field, background, brief summary or the following detailed description.

The invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that the present invention may be practiced in conjunction with any number of data transmission protocols and that the system described herein is merely one exemplary application for the invention.

For the sake of brevity, conventional techniques related to signal processing, data transmission, tomography imaging, EIT electrodes, EIT image reconstruction, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

As used herein, a "node" means any internal or external reference point, connection point, junction, signal line, conductive element, or the like, at which a given signal, logic level, voltage, data pattern, current, or quantity is present. Furthermore, two or more nodes may be realized by one physical element (and two or more signals can be multiplexed, modulated, or otherwise distinguished even though received or output at a common mode).

The following description refers to nodes or features being "connected" or "coupled" together. As used herein, unless expressly stated otherwise, "connected" means that one node/feature is directly joined to (or directly communicates with) another node/feature, and not necessarily mechanically. Likewise, unless expressly stated otherwise, "coupled" means that one node/feature is directly or indirectly joined to (or directly or indirectly communicates with) another node/feature, and not necessarily mechanically. Thus, although the schematics shown in the figures depict example arrangements of elements, additional intervening elements, devices, features, or components may be present in actual embodiments (assuming that the functionality of the circuits and systems are not adversely affected).

FIG. 1 is a schematic representation of an EIT system 100 configured in accordance with an example embodiment of the invention. EIT system 100 is suitably configured to support the EIT techniques described in more detail below. EIT system 100 generally includes a plurality of electrodes 102, a switching network 104, a current source 106, a voltage measurement element 108, an EIT processing unit 110, a suitable amount of memory 111, a display 112, and a user interface ("UI") 114. Although depicted as distinct processing and/or hardware elements, any number of the components shown in FIG. 1 may be combined in a practical embodiment. For example, switching network 104, current source 106, voltage measurement element 108, and EIT processing unit 110 may be combined into a single computing device or diagnostic cabinet. EIT system 100 is capable of evaluating interior features of a body under test 116 (a human body in this example) using electrodes 102 placed on body 116.

EIT system 100 may use any number of electrodes 102 (within practical limitations) to form an electrode array or matrix on body 116. Each electrode 102 is suitably configured to administer a test current to body 116 and to measure a sense voltage generated in response to the test current. The application of the test current and/or the sensing of the measured response voltage may be realized using more than one electrode 102 in a practical embodiment. For example, two electrodes 102 can be utilized to form a circuit for applying the test current and/or for measuring the sense voltage defined between the two electrodes. In a practical embodiment of EIT system 100, each electrode 102 has at least one voltage lead and at least one current lead, where a "lead" may be realized with any number of physical wires, conductors, or the like. In operation, electrodes 102 are attached to body 116 in appropriate locations surrounding the section of body 116 under investigation. For example, electrodes 102 may be placed around the torso of body 116 to enable evaluation of the thoracic cavity.

Electrodes 102 are coupled to switching network 104 to enable the administration of test currents to body 116 and to enable the measurement of sense voltages by EIT system 100. Switching network 104 is suitably configured to designate certain electrodes 102 as source electrodes, sink electrodes, feed points, or the like, during operation of EIT system. In this regard, switching network 104 may utilize a switching algorithm (which may be maintained by EIT processing unit 110, switching network 104, and/or other functional elements of EIT system 100) to perform selective switching of electrodes 102 in the manner described in more detail below. In particular, switching network 104 is preferably configured to establish a virtual short circuit (i.e., virtual shorts) between a designated source electrode and at least one other electrode, other than a designated sink electrode, from the array of electrodes 102. As described below, the creation of a virtual short may be accomplished by maintaining the designated source electrode and the at least one other electrode at the same voltage potential. Switching network 104 may also be configured to direct test current from current source 106 to appropriately switched electrodes 102 serving as source electrodes, and to direct sense voltages from appropriately switched electrodes 102 to voltage measurement element 108.

As mentioned above, current source 106 is coupled to electrodes 102. In the example system shown in FIG. 1, such coupling may be via switching network 104. Current source 106 is suitably configured to provide a test current to the designated source electrode, where the test current has characteristics that produce a sense voltage between the designated source electrode and the designated sink electrode. The amount of test current, the duration of the test current application, modulation of the test current, and other electrical properties of the test current are selected to suit the needs of the particular application, according to the body under test 116, and according to the section of body 116 under investigation.

Voltage measurement element 108 may also be coupled to switching network 104. Voltage measurement element 108 is suitably configured to measure the sense voltage induced by the applied test current. In practice, the measured sense voltage is indicative of the potential across the designated source and sink electrodes. In this regard, switching network 104 is configured such that voltage measurement element 108 is in communication with the voltage leads of the designated source and sink electrodes. As described below, during an EIT procedure, switching network 104 can perform switching of electrodes 102 to allow EIT system 100 to obtain sense voltage measurements for different combinations of source and sink electrodes.

EIT processing unit 110 (and other illustrative blocks, modules, processing logic, and circuits described in connection with the embodiments disclosed herein) may be implemented or performed with a general purpose processor, a content addressable memory, a digital signal processor, an application specific integrated circuit, a field programmable gate array, any suitable programmable logic device, discrete gate or transistor logic, discrete hardware components, or any combination thereof, designed to perform the functions described herein. For example, EIT processing unit 110 may be realized in a conventional personal computer platform having an appropriate amount of processing memory, an appropriate amount of application and data storage space, and a suitably powered processor. A processor may be realized as a microprocessor, a controller, a microcontroller, or a state machine. A processor may also be implemented as a combination of computing devices, e.g., a combination of a digital signal processor and a microprocessor, a plurality of microprocessors, one or more microprocessors in conjunction with a digital signal processor core, or any other such configuration.

Moreover, the steps of a method or algorithm described in connection with the embodiments disclosed herein may be embodied directly in hardware, in firmware, in a software module executed by a processor, or in any practical combination thereof. A software module may reside in RAM memory, flash memory, ROM memory, EPROM memory, EEPROM memory, registers, a hard disk, a removable disk, a CD-ROM, or any other form of storage medium known in the art. In this regard, an exemplary storage medium can be coupled to a processor such that the processor can read information from, and write information to, the storage medium. In the alternative, the storage medium may be integral to the processor. As an example, the processor and the storage medium may reside in an ASIC.

As described in more detail herein, EIT processing unit 110 supports the operation of EIT system 100. For example, EIT processing unit 110 may be coupled to switching network 104 to receive test currents and sense voltage measurements generated during EIT procedures. In particular, EIT processing unit 110 can obtain current data indicative of test current, along with voltage data indicative of sense voltage, for processing and analysis. EIT processing unit 110 performs a reconstruction procedure, which is based upon the current and voltage data, to obtain the desired electrical characteristics of the interior features of body 116. For example, EIT processing unit 110 processes the information received from electrodes 102 to determine an impedance profile for a section of the body under test, where that section is located between electrodes 102.

Using suitable imaging and display techniques, EIT processing unit 110 can generate an image file for the impedance profile, and render that image file on display 112 for viewing by a technician or operator of EIT system 100. Practical embodiments of EIT system 100 include user interface 114, which is used by the operator. User interface 114 may include, without limitation: a keyboard, buttons, lights, a speaker, a touchpad, a touch screen, a pointing device such as a mouse or a trackball, or the like. Although not shown in FIG. 1, EIT system 100 may also include a printer coupled to EIT processing unit 110. Moreover, EIT system 100 may support network connectivity using conventional computer network technologies to accommodate the transmission of data and test results to remote computing devices.

The EIT method described herein channels an electrical current to a greater extent than past approaches in EIT. This technique uses virtual shorts to evaluate the conductivity profile within a measured object. This method also uses virtual shorts to evaluate the resistance through a section of an object. The resistance through a section of the object is evaluated by measuring the voltage across the section of the object divided by the current flowing through that section of the body. The voltage and current measurements through that section of the body both have better resolution and greater distinguishability than earlier measurement approaches to EIT. Improved resolution and greater distinguishability also provides improved imaging capability.

Figure 2:
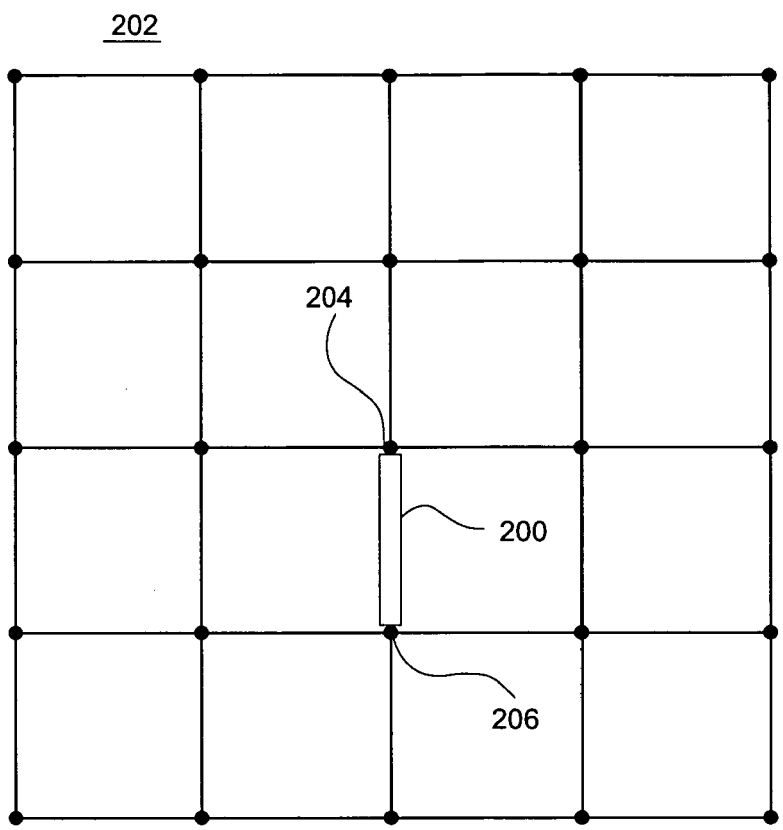
FIG. 2 is a diagram of an embedded resistor in a resistive network.
Figure 3:
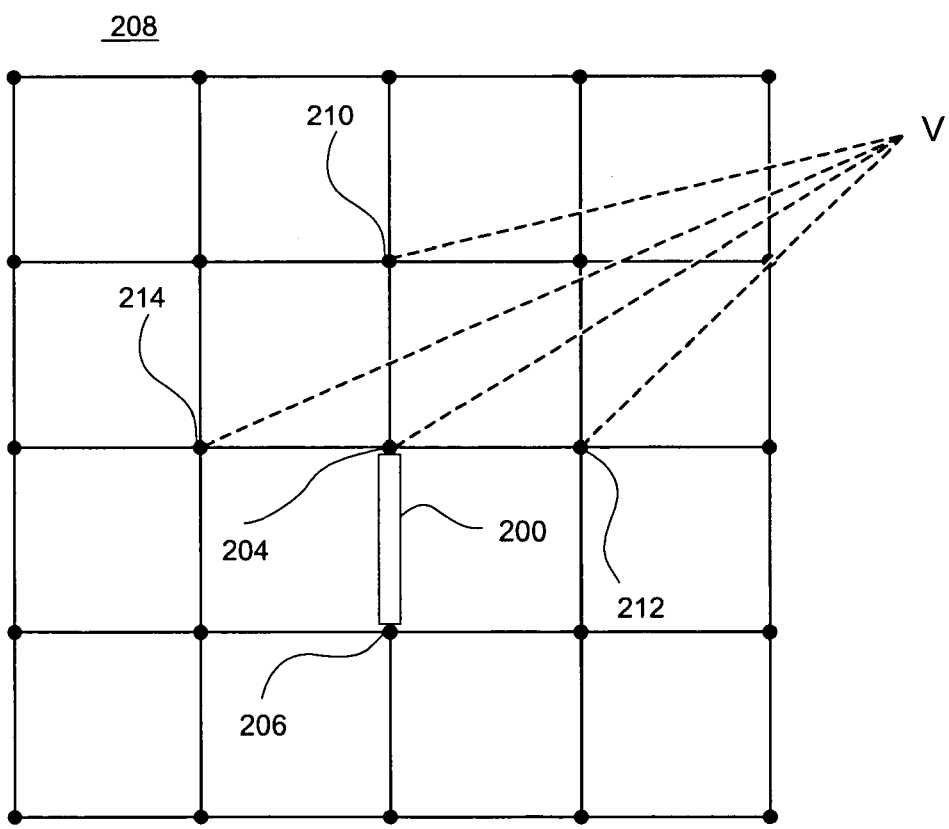
FIG. 3 is a diagram of an embedded resistor in a virtually shorted resistive network.

A simple resistor network problem is shown in FIG. 2, which is a diagram of an embedded resistor 200 in a resistive network 202. The grid intersection points in FIG. 2 represent points, where the section of the network between any two grid points has an impedance. Here, it is desired to measure the resistance of a discrete embedded resistor 200. The difficulty in taking a four point resistance measurement at the two end points of resistor 200 is that the current will not only flow through resistor 200 but through the rest of the network 202. With the other resistors in the rest of the network 202, there does not appear to be any practical way to measure the resistor 200 without including the resistance from the rest of the network 202. However, the resistor 200 can be measured if current flowing from the source point 204 to the sink point 206 is removed (except through the resistor 200). This can be accomplished by introducing a virtual short into the network 200. FIG. 3 depicts such a "virtually shorted" network 208.

In network 208, source point 204, the top sink point 210, the right sink point 212, and the left sink point 214 are held at the same potential (V). The dashed lines in FIG. 3 represent the virtual short between source point 204 and the three sink points. Since these points are all at the same potential, all current from the source point must flow to the bottom sink point 206 through the resistor 200. If the voltage difference between the source point 204 and the bottom sink point 206 can be measured, and if the source current (or equivalently through the leg connected to the sink point and resistor under test) can be measured, the resistance of the resistor 200 can be derived.

Figure 4:
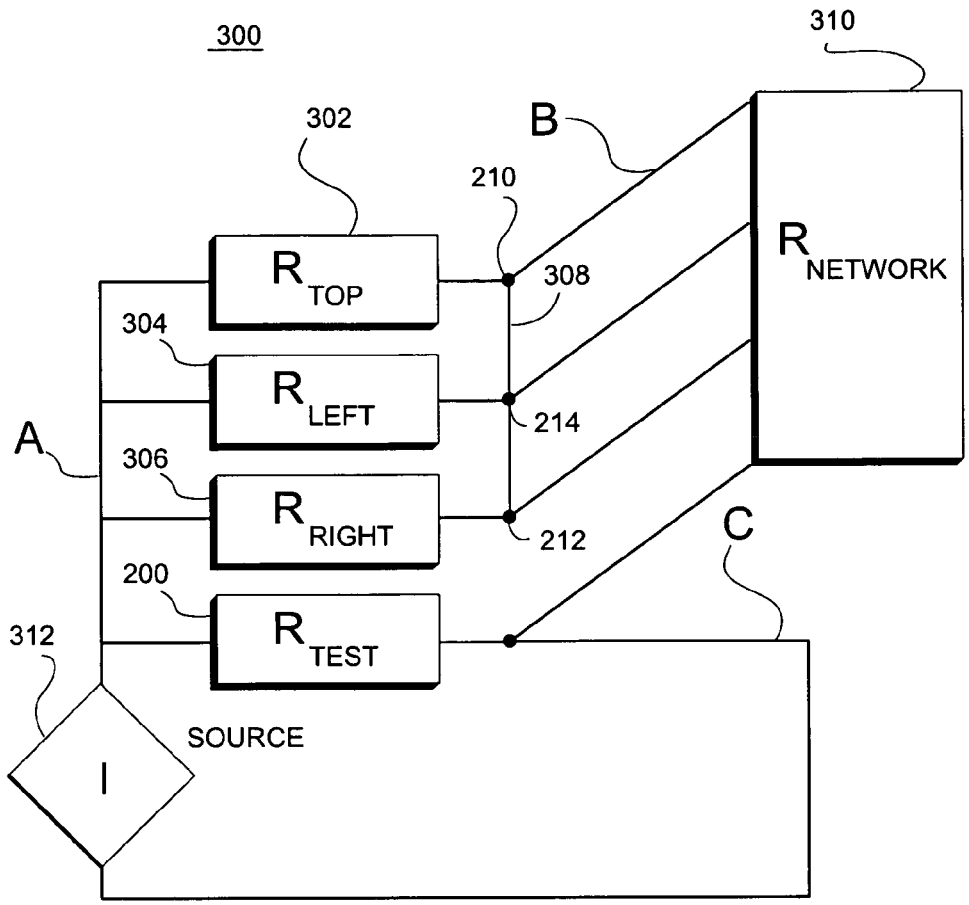
FIG. 4 is a schematic diagram of a circuit with shorted feed points corresponding to the virtually shorted resistive network shown in FIG. 3.
Figure 5:
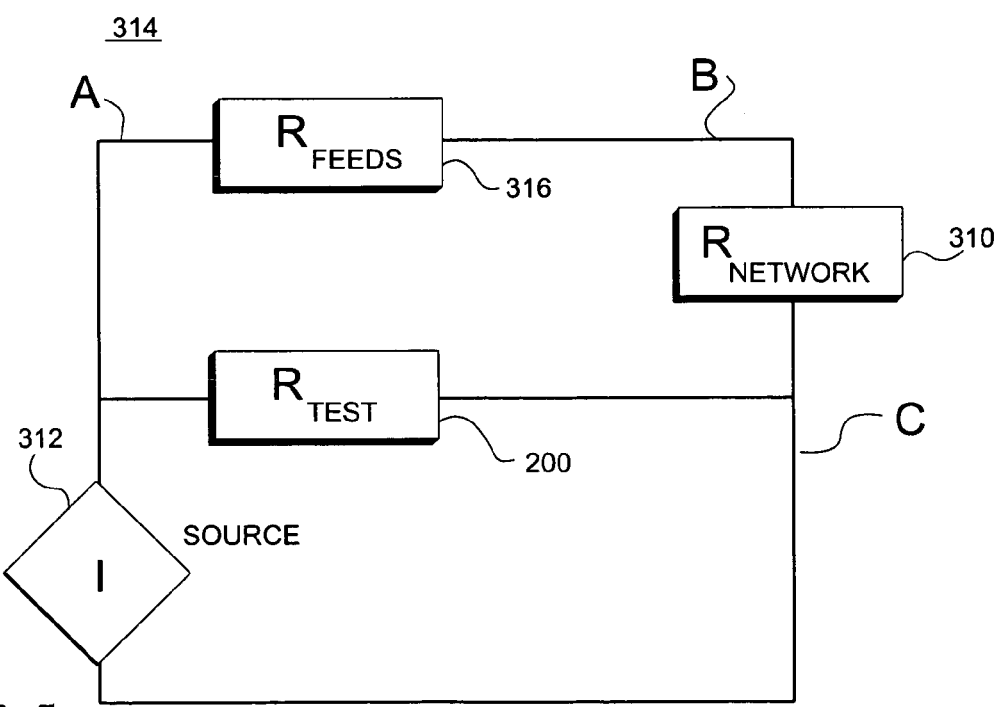
FIG. 5 is a schematic diagram of a circuit that is equivalent to the circuit shown in FIG. 4.

The network 202 in FIG. 2 is assumed to have a source point 204 at the same point shown in FIG. 3. Network 202 can be reduced to network 208 (see FIG. 3) in the following manner. First the top, right and left feeds are shorted together, as depicted in FIG. 4. The circuit 300 of FIG. 4 includes the resistor under test 200, a top resistor 302 corresponding to the section between source point 204 and top sink point 210 in FIG. 3, a left resistor 304 corresponding to the section between source point 204 and left sink point 214, and a right resistor 306 corresponding to the section between source point 204 and right sink point 212. In FIG. 4, a conductive lead 308 is connected to all three sink connection points; this common node is labeled B in FIG. 4. The remainder of the resistive network is depicted as a combined network resistance 310 in FIG. 4. A current source 312 represents the test current applied to resistor 200 by circuit 300. The circuit 300 of FIG. 4 can be simplified to the form shown in FIG. 5, where circuit 314 includes nodes A, B, and C corresponding to the same node labels shown in FIG. 4. Notably, circuit 314 lumps top resistor 302, left resistor 304, and right resistor 306 together into a feed resistor 316. As shown in FIG. 5, feed resistor 316 is coupled between nodes A and B, while resistor under test 200 is coupled between nodes A and C. Referring to FIG. 3, node A corresponds to source point 204, and node C corresponds to sink point 206.

Again, the goal is to maintain an identical voltage potential across both sides of the feed resistor 316. In practice, this can be accomplished with an operational amplifier. It is well known that an ideal operational amplifier modifies its output in such a way that its two input leads are held at the same potential (i.e., a virtual short is created across the input leads). In addition, no current flows through the input leads of an ideal operational amplifier. Therefore, by placing the input leads of an operational amplifier at nodes A and B of circuit 314, the potential across the combined feed resistor 316 will be held at the same potential.

Figure 6:
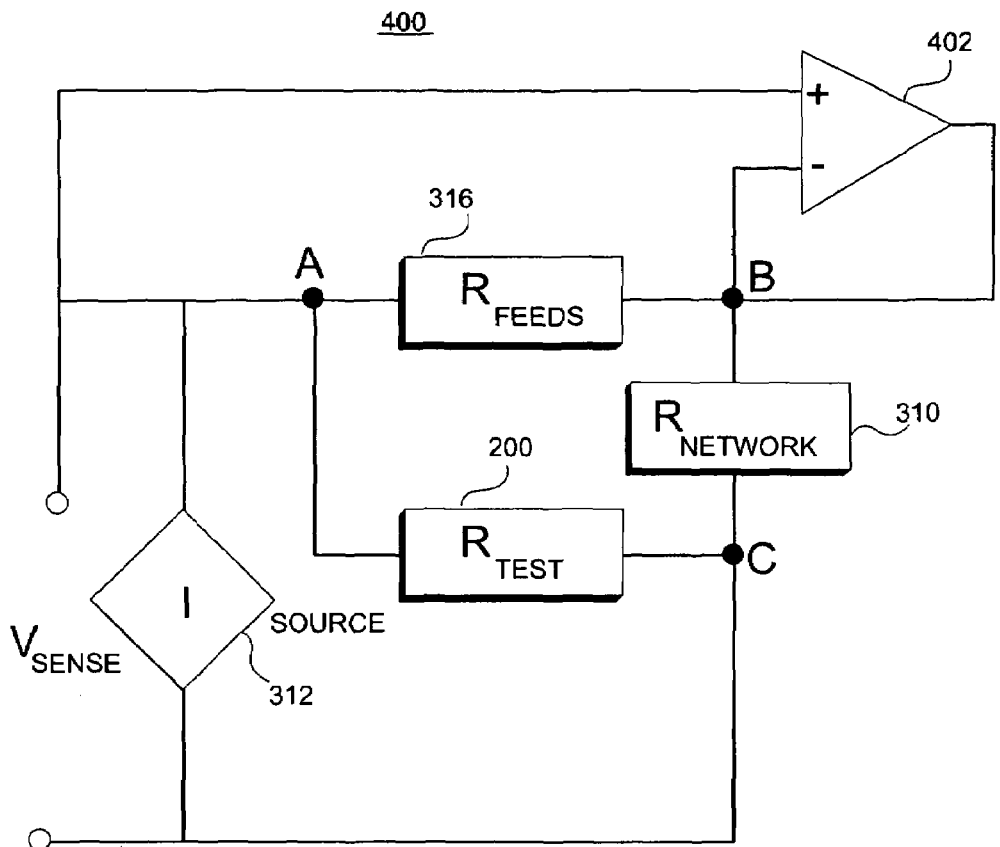
FIG. 6 is a schematic diagram of a circuit that employs an operational amplifier to establish virtual shorts.

FIG. 6 is a schematic of a circuit 400 that employs an operational amplifier 402 to establish virtual shorts. Circuit 400 represents circuit 314 with operational amplifier 402 inserted to achieve the virtual short as described above. One input (the positive feed in this example) to operational amplifier 402 corresponds to node A, the other input to operational amplifier 402 corresponds to node B, and the output of operational amplifier 402 feeds back to node B. FIG. 6 shows that the sense voltage is measured across nodes A and C.

This technique of measuring a test resistor is known as 6-wire ohms measurement, and is sometimes referred to as a voltage follower technique. This process can also be called "guarding out" because the resistors at the feeds are effectively blocked. A similar technique is described in the context of resistance measurement test equipment in "Configuring a Resistor Network Test System with the Model 2400 SourceMeter® Instrument," Keithly Instruments, Inc. (2001), the content of which is incorporated by reference herein.

In the manner described above, a localized impedance can be evaluated by placing a current source at one end of the resistance under test and a sink at the other end of the resistance with the other paths held at the same potential as the current source, thus removing contaminating shunt resistance. This is analogous to the problem found in conventional EIT systems, where shunt currents significantly reduce the effect of the resistive anomalies within an object.

In this example, an additional point to the resistive network referred to as the sink point is added (in practice, the sink point corresponds to one of the EIT electrodes). As explained above in connection with FIG. 6, no current flows between the source point and the common feed points due to the virtual short architecture. The current at the feed points and at the source point has only one outlet: the sink point. In operation, a test current will be specified through the source point. Additional current will flow through the feed points to the sink point. The system measures the voltage potential between the source point and sink point, and the resistance of the resistor under test is the voltage potential divided by the current through the source point. In an EIT application, the following practical considerations are taken: (1) there are a number of electrodes all held at the same potential; (2) there is a specified current through a source point that flows through a localized section of the network to a sink point; and (3) the resistance of the localized section can be evaluated in isolation from the rest of the resistances in the network.

Therefore, applying virtual short techniques can improve EIT measurements. In conventional EIT measurements, a number of currents are induced on an object under study through applied electrodes and voltages over another set (or possibly the same set) of electrodes are measured. For the virtual short implementation, an entirely different approach is taken. In particular, the EIT system imposes a unit current through a single electrode (the source electrode) and let currents at a number of different electrodes be constrained so that their potential is the same as the potential of the source point. The system then measures the voltage from the source point to a sink point. Notably, instead of specifying the current distribution at each electrode, the EIT system specifies the voltage at each electrode (except for the sink point).

Applying the Virtual Short Measurement Technique to Some Simple Examples

Figure 7:
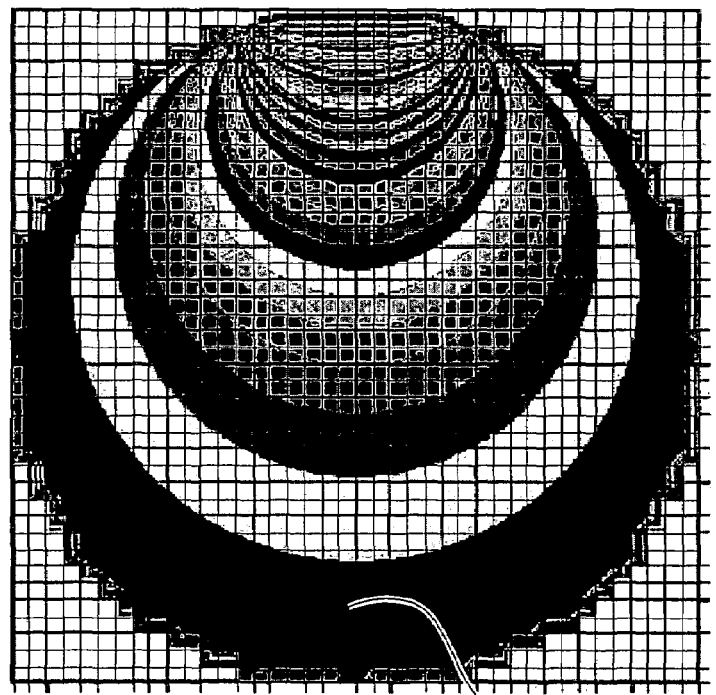
FIG. 7 is a graph of equipotential regions within a cylindrical body having a unit voltage sink located at the top of the circle.

FIG. 7 is a graph of equipotential regions within a cylindrical body having a unit voltage sink located at the top of the circle (FIG. 7 depicts a cross section of the cylindrical body). This body does not include any virtually shorted points. This circular cylinder has a unit voltage distributed over a 20 degree angle sink located at the top of the circle. Over this section a unit voltage is specified; over the rest of the circle, the potential is held to zero. The circle has a homogenous surface resistance of 1 ohm/square. FIG. 7 also represents the current flowing in the circular cylinder. Current flows in the direction orthogonal to the equipotential lines shown in FIG. 7, where the equipotential lines are defined in 0.025 volt steps. Thus, the equipotential region 500 represents a voltage that is close to zero, while the equipotential regions near the top of the circle represent voltages that increasingly approach one volt. For a sink placed at the bottom of the circle, only a relatively small amount of current flows from this sink to the source. The current distribution through the source is 0.056129 amp per unit length versus 1.8 amps per unit length through the sink. Again, the principal measurement is resistance, which is the unit voltage divided by current times the length of electrode.

Figure 8:
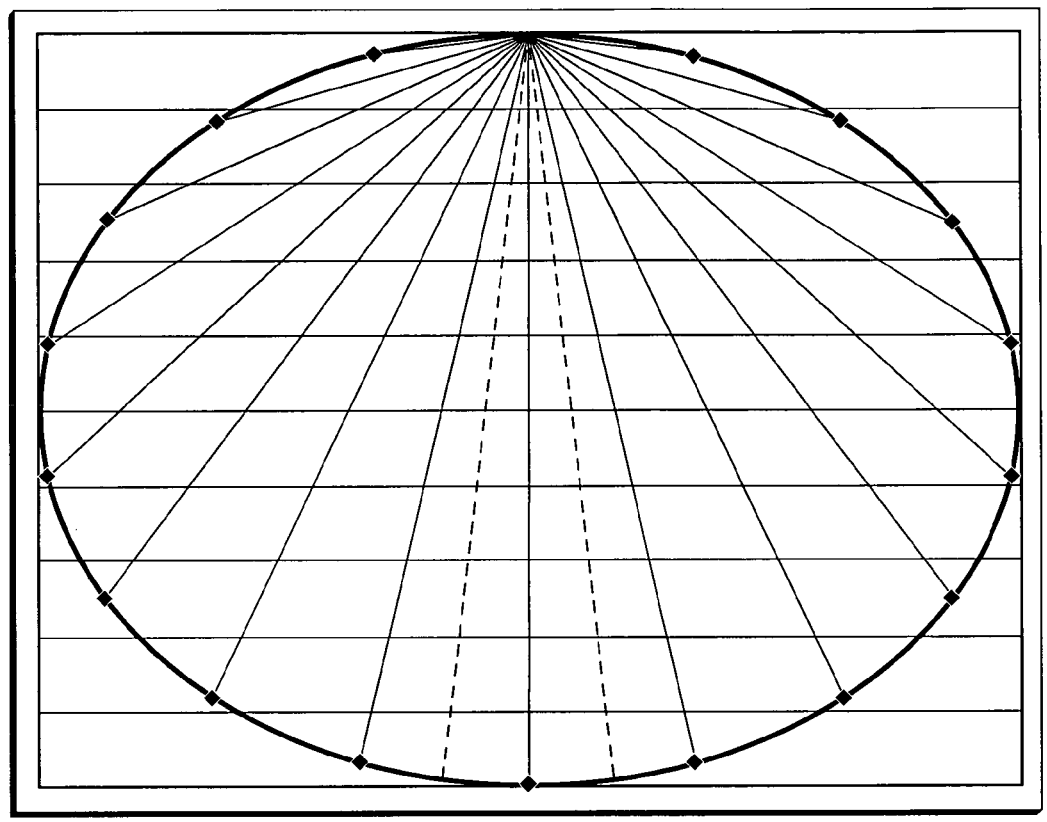
FIG. 8 is a graph that depicts a rough approximation of the behavior of a cylindrical body having virtually shorted feed points.

FIG. 8 is a graph that depicts a rough approximation of the behavior of a cylindrical body having virtually shorted feed points. FIG. 8 represents a cross sectional view of a body under test, where the perimeter of the circle represents the exterior surface of the body under test. In FIG. 8, a unit voltage is placed at the source point at the top of the circle, and zero voltage is held at the sink point on the bottom of the circle and at each of the feed points around the outer surface of the cylinder. The approach of using a virtual short channels the electric current through a narrower section of the object under test. In contrast, the current flow depicted in FIG. 7 is more dispersed throughout the cylinder. The dashed lines in FIG. 8 indicate the channel of concentrated current flow. This implies that when a resistance is placed in this path the resistance will change by a larger amount than if the current has not been channeled.

Figure 9:
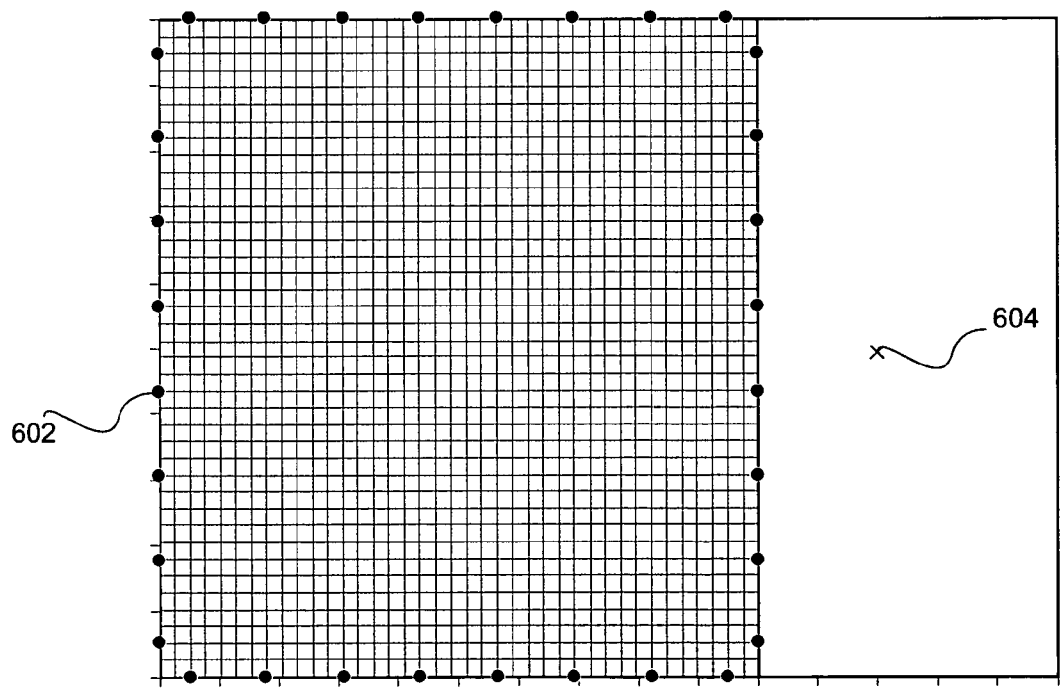
FIG. 9 is a diagram of a resistive network having a rectangular grid topology.

Of course, EIT can be applied to a number of different geometries, and the virtual short methodology can be utilized with geometries other than cylindrical bodies. For example, FIG. 9 is a diagram of a resistive network 600 having a rectangular grid topology. The number of nodes in resistive network 600 is arbitrary for this example. Each node is separated by a 1 ohm discrete resistor. Eight electrode points are placed on each exterior side of the rectangular grid. A single source point 602 is placed approximately in the center of one of the sides of the rectangular grid. This example considers a sink point 604 that is opposite the source point 602. For the calculations, the source and the remaining feed points are all shorted together (a nominal resistor of $1.0 \times 10^{-8}$ ohms is placed between the points). The sink point 604 is also connected to the feed points via a large resistor of $1.0 \times 10^8$ ohms to simulate an open for programming convenience.

There are different configurations possible for feed points. For the rectangular grid, the following configurations are considered: (1) feed points at all available points; (2) feed points at all points on the same side as the source point 602; (3) feed points at the opposite side as the source point 602; and (4) no feed points. Configuration (4) corresponds to the standard approach used in conventional EIT systems. Note that by reducing the number of feed points, the measured resistance decreases.

Figure 10:
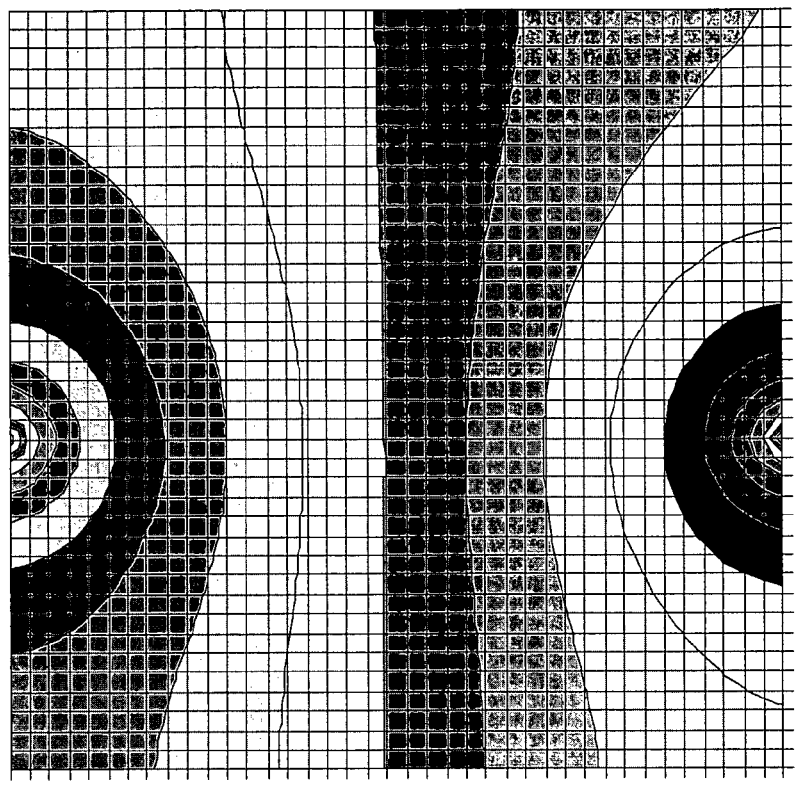
FIG. 10 is a voltage mapping of equipotential regions for the rectangular grid topology shown in FIG. 9, where feed points are not virtually shorted.
Figure 11:
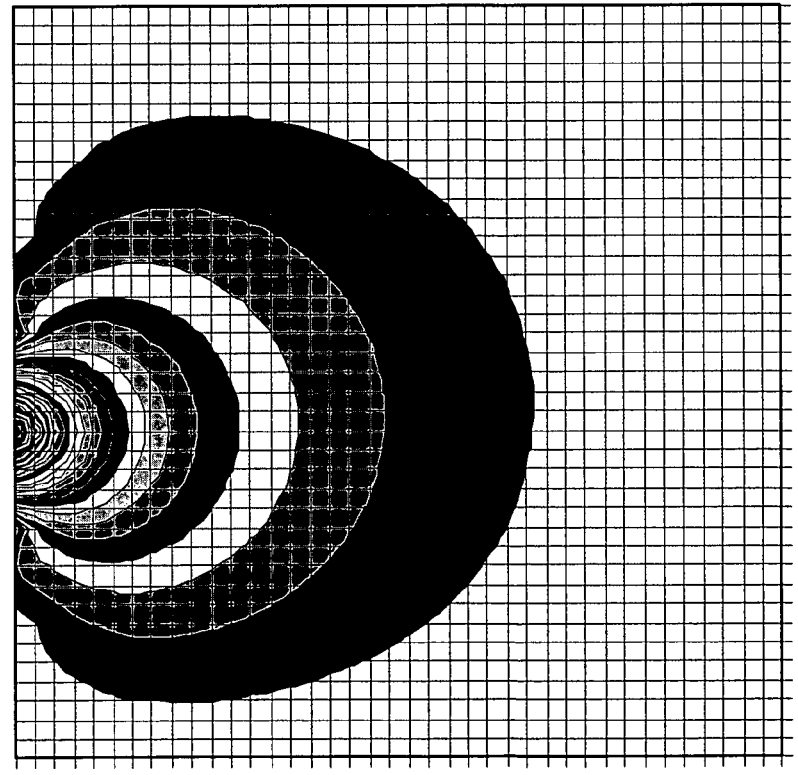
FIG. 11 is a voltage mapping of equipotential regions for the rectangular grid topology shown in FIG. 9, where feed points are virtually shorted.

The current flow using a virtual short and for the standard method are very different. In this regard, FIG. 10 is a voltage mapping of equipotential regions for the rectangular grid topology shown in FIG. 9, where feed points are not virtually shorted, while FIG. 11 is a voltage mapping of equipotential regions for the rectangular grid topology shown in FIG. 9, where feed points are virtually shorted. FIG. 11 has a voltage scale with steps of 0.025 volts with an overall range from 0.0 to 1.0 volts. The voltage mapping depicted in FIG. 10 has a range from 0.0 to 3.0 volts, with step sizes of 0.125 volts. Comparing FIG. 10 to FIG. 11, the current distribution is much more directed from the source to the sink for the virtual short configuration.

Figure 12:
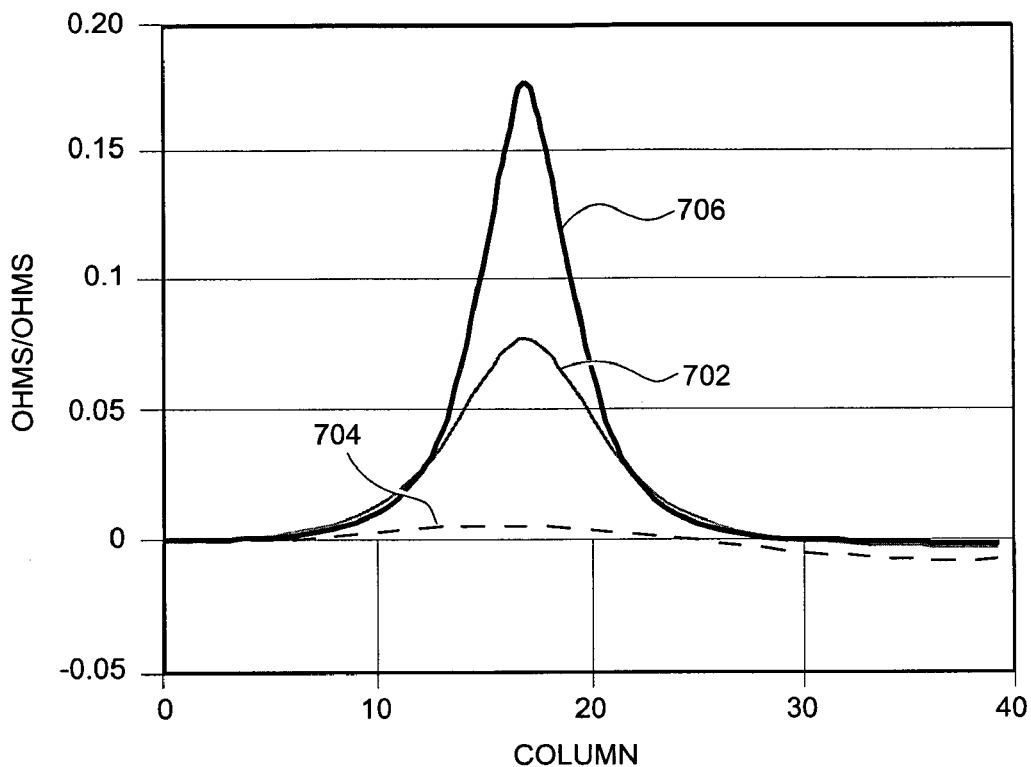
FIG. 12 is a graph showing the effect of resistance perturbation for the rectangular grid topology shown in FIG. 9, where feed points are not virtually shorted.
Figure 13:
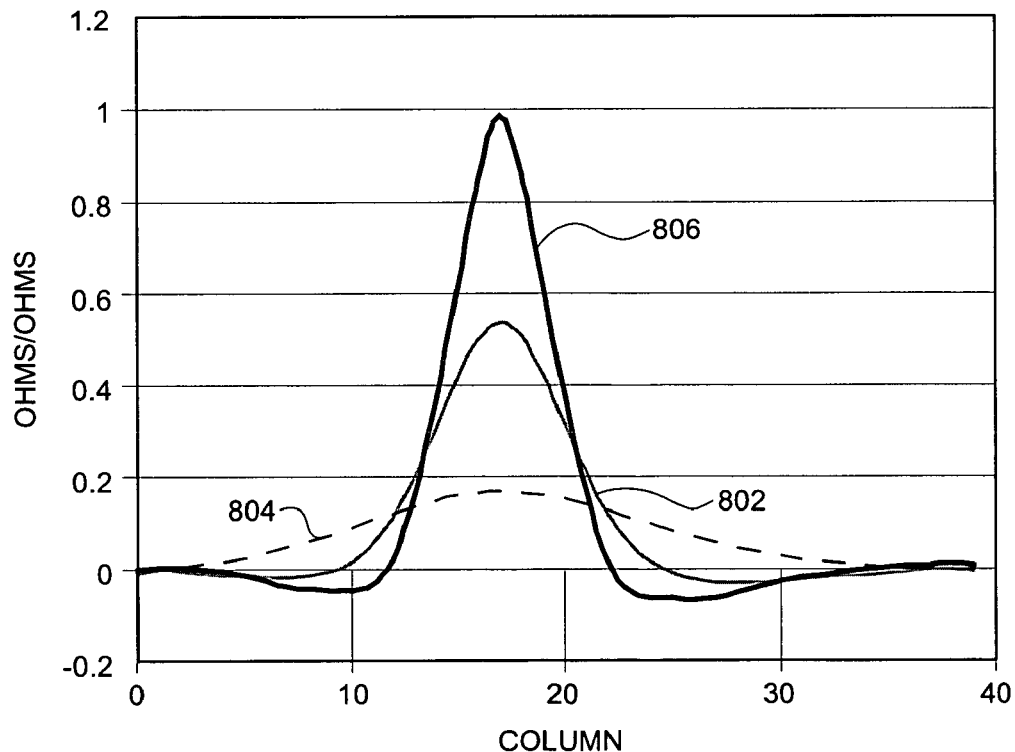
FIG. 13 is a graph showing the effect of resistance perturbation for the rectangular grid topology shown in FIG. 9, where feed points are virtually shorted.

In practice, the goal of an EIT system is to distinguish changes in impedance within the body under test. Accordingly, it is desirable to have an EIT system that can distinguish impedance changes at an appropriate resolution. Consider a horizontally directed resistive segment with a raised resistance. Referring to the grids of FIG. 10 and FIG. 11, the following considers the segments at 5, 19, and 35 points away from the source point. The change in measured resistance (voltage difference between source and feed point divided by input current through source) can be plotted as the change in resistance moves through each row in the grid. FIG. 12 is a graph showing the effect of resistance perturbation for a rectangular grid topology using configuration (4) discussed above, where feed points are not virtually shorted. In contrast, FIG. 13 is a graph showing the effect of resistance perturbation for a rectangular grid topology using configuration (1) discussed above, where all feed points are virtually shorted together. The vertical scale in FIG. 12 and FIG. 13 represents the percentage change in resistance due to a 1.0 ohm perturbation (for example, one of the resistances between a source and sink point has changed from 1.0 ohm to 2.0 ohms). In FIG. 12, plot 702 corresponds to segment/column 5, plot 704 corresponds to segment/column 19, and plot 706 corresponds to segment/column 35. In FIG. 13, plot 802 corresponds to segment/column 5, plot 804 corresponds to segment/column 19, and plot 806 corresponds to segment/column 35. In this example, the source and sink points are located 17 segments away from the bottom of the grid. The largest change in the resistance occurs when this resistive perturbation is at row 17. The maximum resistive perturbation is a 1.0 ohm increase with the network composed already of 1.0 ohm resistors.

There is a dramatic increase in the distinguishability using the virtual short measurement over the standard measurement. The virtual short method detects a resistance change by a factor of 6.9, 30.7 and 5.6 greater than the standard method for columns 5, 19, and 35, respectively. If the assumed accuracy of the measurement is 0.02%, the standard technique will not detect the perturbation but the virtual short method will. FIG. 12 and FIG. 13 indicate that the virtual short method and standard method both have their greatest difficulty measuring an object deep in the interior of the network.

Similar measurements and resistance perturbation characteristic plots can be obtained for configuration (2) and configuration (3) discussed above. Such measurements reveal that configuration (1) outperforms configuration (2), and that configuration (2) outperforms configuration (3). These measurements all assume that there is 1.0 amp flowing through the sink point. In practical embodiments, the current through the source point can be detected even when current flowing through the sink point is as low as 1.0 mA. Indeed, some existing measurement systems can readily measure currents to very low levels, e.g., measurements within 0.03% accuracy with values less than 100 pA.

An important consideration is the total power expended for both the power supply and for the object under test. In this regard, the power expended by each of these approaches can be compared. Because the additional electrode pads provide additional conductors to the EIT system, the power used by configuration (1) is less than the power used by configuration (2), which is less than the power used by configuration (3), which is less than the power used by configuration (4). If, however, the power is assumed to be the same to all configurations, then the voltage from the feed points to the sink point must be scaled by the square root. This leads to a distinguishability factor value of 50 between the configuration (1) measurement and the configuration (4) measurement.

Notably, all of the configurations outperform the standard ("point to point") measurement technique. Configuration (1), where all feed points are virtually shorted, performs the best and uses the least amount of power. This configuration also has the least amount of current through the source electrode, although this should not be a practical constraint. If the low source current becomes a constraint, then the other configurations can be used with some loss in performance. These configurations all significantly outperform the standard measurement.

Another example geometry that may be considered is the circle or cylinder. For example, a homogeneous 100 ohm/square circle with electrode points around the circumference, and the same circle with a conductive inner core can be analyzed. Significant improvement is obtained with this topology—by a factor of 8 for the virtual short measurement technique versus the standard measurement technique (and by a factor of 16 when power compensated). In practice, other current patterns can be used for EIT. These improved current patterns show approximately a three-fold improvement over the point to point measurement used here. These optimal current patterns require more power than the point to point and so are only improved by a factor of approximately 1.5 when power compensated. The virtual short technique provides improved distinguishability even over these other current patterns.

Some Practical Considerations

In practical embodiments, there are a number of errors within measurements using a virtual short. The errors of concern are errors that are involved with DC voltage measurement and errors that are associated particularly with the characteristics of the operational amplifier used by the EIT system. Errors associated with the DC voltage measurement include noise and stability. These are issues present in conventional EIT measurement systems. As mentioned above, an operational amplifier is utilized by an EIT configured in accordance with the invention. Practical sources of errors in an operational amplifier include: (1) the voltage offset; (2) the input bias current; (3) the common mode rejection ratio; and (4) limited guard output current.

Figure 14:
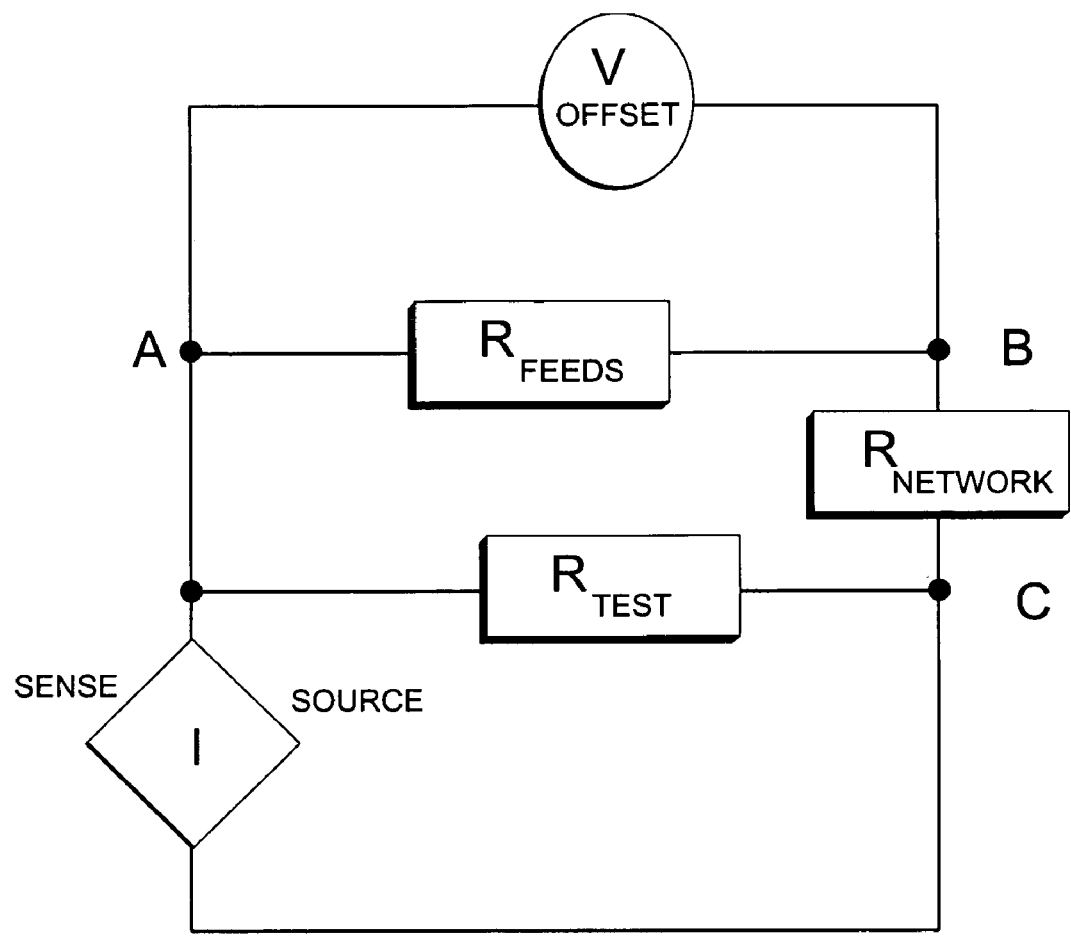
FIG. 14 is a circuit diagram that depicts voltage offset error in a resistive network that employs virtual short measurement techniques.

FIG. 14 is a circuit diagram that depicts voltage offset error in a resistive network that employs virtual short measurement techniques. In the example embodiment described above in connection with FIG. 6, the voltage offset is the voltage difference across the input leads to the operational amplifier. This offset error leads to a potential difference between the source and the feed electrodes. This in turn drives a current between these two points. This current lowers the current flowing through the resistor under test, leading to a lower measured voltage between source and sink and lowered calculated resistance. The percent error in the resistance is given by:

$$\frac{\Delta R}{R} = \frac{V_{offset}}{R_{feeds} I_{test}}.$$

In practice, there will be a maximum amount of test current ($I_{test}$) because only a limited amount of current will be driven through the operational amplifier (e.g., less than 1.0 mA). The relationship between current through the test resistor and the total current through the operational amplifier is given by: $R_{test} I_{test} = R_{network} I_{max}$. Consequently, the following expression relates the percent error in resistance to the maximum current:

$$\frac{\Delta R}{R} = \frac{R_{test} V_{offset}}{R_{feeds} R_{network} I_{max}}.$$

Typical offset voltage values are in the tens of microvolts. This error can be reduced in at least two different ways. The value for the unknown resistance in terms of a measured voltage, measured current, offset voltage and feed resistance is given by:

$$R_{test} = \frac{V_{measured}}{I_{measured} - \frac{V_{offset}}{R_{feeds}}}.$$

A reasonably accurate evaluation of $R_{feeds}$ can be obtained by taking a measurement with no nodes (source, feed, or sink nodes) shorted. In addition, the offset voltage can be reduced by applying a potentiometer to the input lines of the voltage amplifier. The error would then be reduced to the random error of the offset voltage which is typically less than 1.0 microvolts. In practical embodiments, the offset voltage may introduce additional complications that can be readily compensated for using known electronic circuit techniques.

Imaging

As explained above, the virtual short measurement technique has greater distinguishability than conventional EIT measurement techniques. The virtual short measurement technique can utilize a suitable imaging tool that uses the measurement information provided by the virtual short technique. For example, with L electrodes, each electrodes can be treated as a source and measure the virtually shorted resistance to the sink. This results in (L)(L−1) measurements. The same measurement is obtained if the source and sink electrodes are swapped, therefore, only (L)(L−1)/2 measurements need be taken in a practical implementation.

Figure 15:
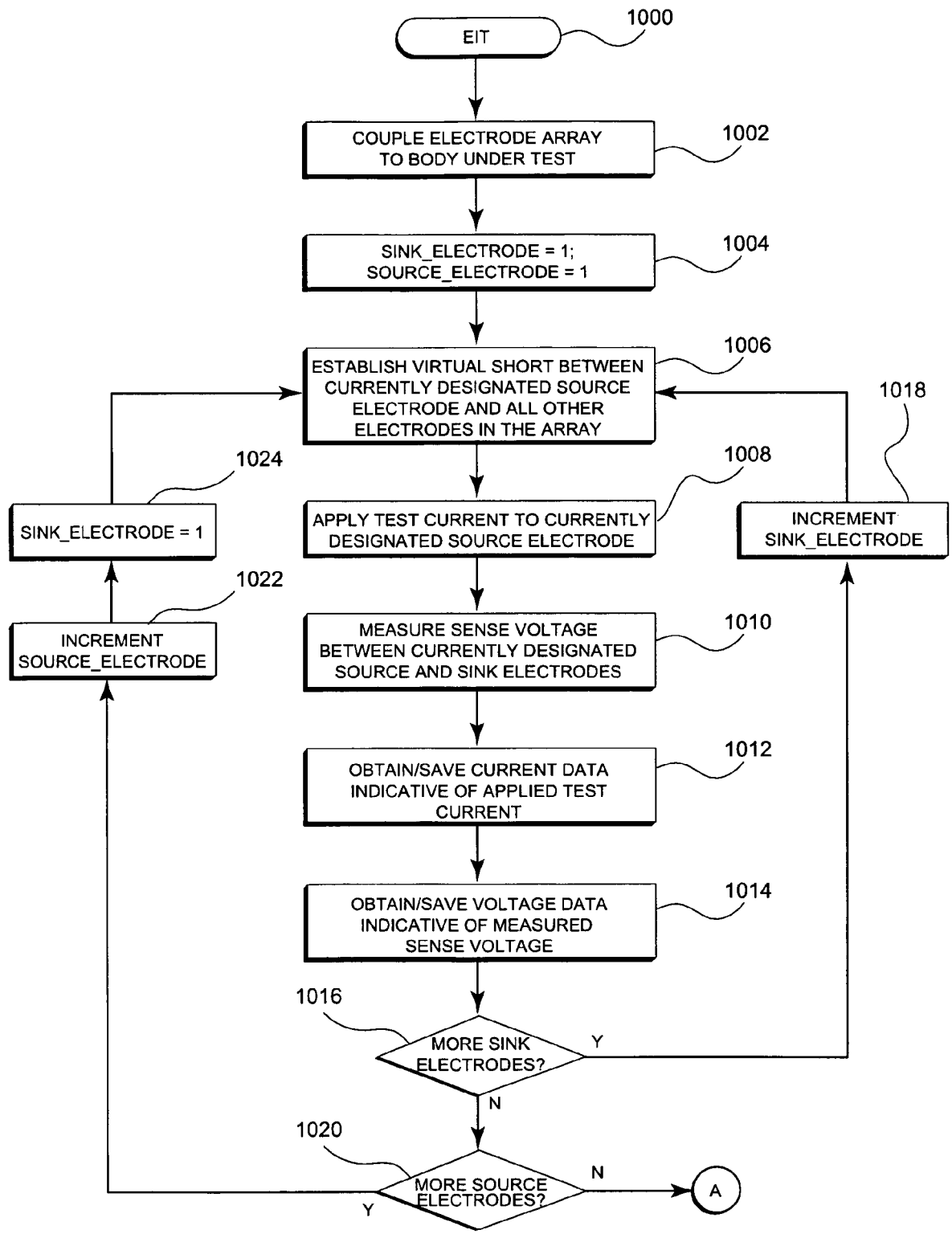
FIG. 15 and FIG. 16 depict a flow chart of an EIT process that may be performed by an EIT system configured in accordance with an example embodiment of the invention.
Figure 16:
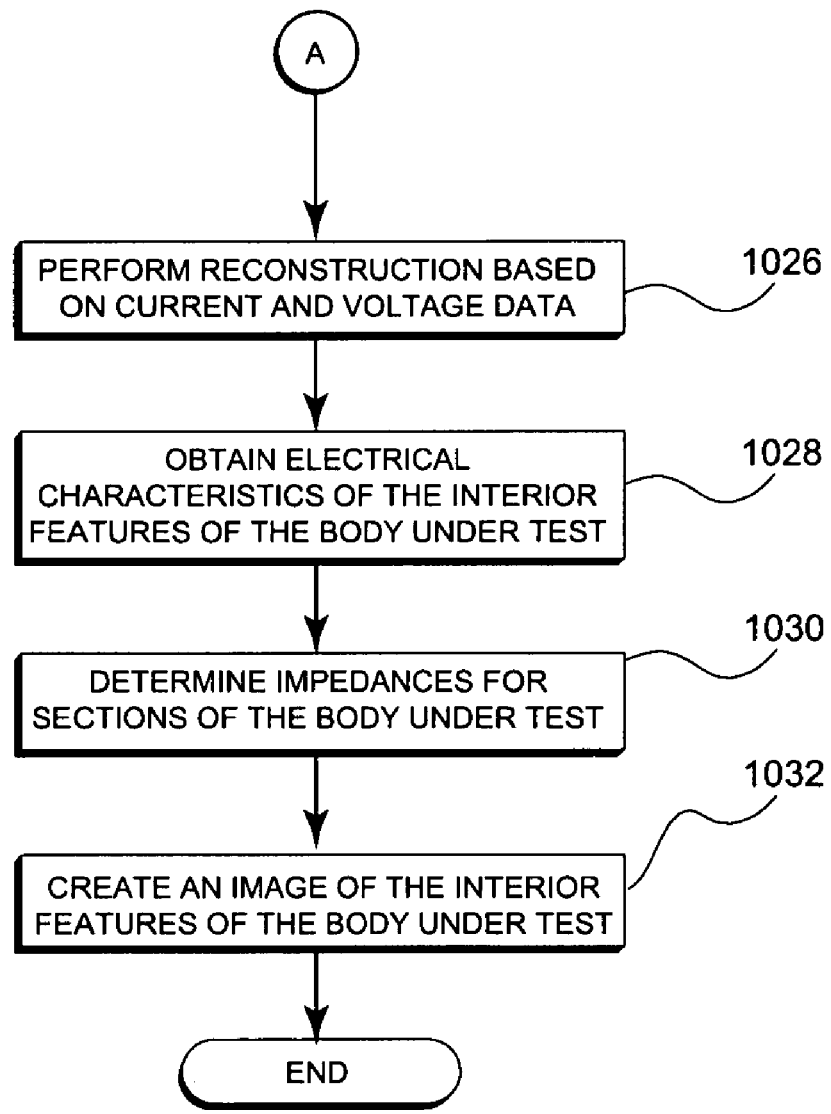

An EIT system configured in accordance with an example embodiment of the invention may be utilized during an EIT procedure to obtain EIT images. In this regard, FIG. 15 and FIG. 16 depict a flow chart of an EIT process 1000 that may be performed by an EIT system configured in accordance with an example embodiment of the invention. The various tasks performed in connection with process 1000 may be performed by software, hardware, firmware, or any combination thereof. For illustrative purposes, the following description of process 1000 may refer to elements mentioned above in connection with one or more of FIGS. 1-14. In practical embodiments, portions of process 1000 may be performed by different elements of the described system, e.g., EIT processing unit 110, switching network 104, electrodes 102, current source 106, or other components shown in FIG. 1. It should be appreciated that process 1000 may include any number of additional or alternative tasks, the tasks shown in FIGS. 15 and 16 need not be performed in the illustrated order, and process 1000 may be incorporated into a more comprehensive procedure or process having additional functionality not described in detail herein.

EIT process 1000 may begin with an operator coupling a plurality of electrodes to the body under test (task 1002). As mentioned above, the electrodes may form an array or a matrix surrounding the section of the body under investigation. EIT process 1000 may initialize a sink electrode count or identifier and a source electrode count or identifier (task 1004). In practice, task 1004 designates one of the plurality of electrodes as a source electrode and another one of the plurality of electrodes as a sink electrode for this processing iteration. Task 1004 may be performed to enable EIT process 1000 to manage the different combinations of source and sink electrodes, and the respective measurements associated therewith. In this example, a "sink_electrode" field is initialized to 1, and a "source_electrode field is initialized to 1. Of course, any suitable identification and designation technique may be utilized in a practical implementation of the EIT system.

Next, the switching network is suitably controlled to establish a virtual short between the currently designated source electrode and at least one of the plurality of electrodes other than the currently designated sink electrode (task 1006). In this example, the virtual short is established between the designated source electrode and all other electrodes in the array other than the designated sink electrode. As described above, the EIT system may manipulate the switching network and utilize an operational amplifier to maintain all of the non-source electrodes at an identical voltage, thus creating the virtual short.

Once the virtual short has been established, EIT process 1000 applies a test current to the designated source electrode (task 1008). In response to this test current, a sense voltage is produced across the resistance under test (which corresponds to a section of the body between the designated source and sink electrodes). The EIT system can then measure the sense voltage between the currently designated source and sink electrodes (task 1010) for the applied test current. In practice, the application of the test current and the measurement of the sense voltage for a given combination of source and sink electrodes represents one measurement iteration of EIT process 1000. The EIT system can obtain/store current data indicative of the applied test current (task 1012) and obtain/save voltage data indicative of the measured sense voltage (task 1014). The current and voltage data is preferably stored for subsequent processing and image rendering as necessary.

If the currently designated source electrode is to be combined with a different sink electrode for a new measurement, then query task 1016 leads to a task 1018, which causes the EIT system to increment the sink_electrode field to designate a new sink electrode. In this example, the next iteration updates the sink_electrode field to a value of 2. After designating a new sink electrode, tasks 1006, 1008, 1010, 1012, and 1014 are repeated to allow the EIT system to obtain and store measurement data for the new combination of source and sink electrodes (source_electrode=1; sink_electrode=2). As depicted in FIG. 15, EIT process 1000 loops in this manner until the desired number of sink electrodes have been combined with the currently designated source electrode. In one practical embodiment, EIT process 1000 repeats the measurement tasks for all available sink electrodes (as mentioned above, if source and sink electrodes are reversed and re-designated as sink and source electrodes, respectively, the measurement need not be repeated).

If there are no more sink electrodes to be tested with the currently designated source electrode, then query task 1016 leads to a query task 1020, which determines whether EIT process 1000 needs to continue for a different source electrode. Thus, if more source electrodes remain, query task 1020 leads to a task 1022, which causes the EIT system to increment the source_electrode field to designate a new source electrode (in this example, the next iteration updates the source_electrode field to a value of 2. In addition, the sink_electrode field is initialized to a value of 1, which may arbitrarily correspond to any one of the electrodes in the array (other than the currently designated source electrode). After designating a new source electrode, tasks 1006, 1008, 1010, 1012, 1014, and 1016 are repeated to allow the EIT system to obtain and store measurement data for the different combinations of the currently designated source electrode and various sink electrodes. As depicted in FIG. 15, EIT process 1000 loops in this manner until the desired number of source electrodes have been combined with the desired number of sink electrodes. In one practical embodiment, EIT process 1000 repeats the measurement tasks for all possible combinations of source and sink electrodes (as mentioned above, if source and sink electrodes are reversed and re-designated as sink and source electrodes, respectively, the measurement need not be repeated). A practical embodiment of the EIT system need not utilize the loop and iteration scheme shown in FIG. 15, and EIT process 1000 is merely one suitable realization of the techniques described in more detail above.

If no additional source electrodes remain (query task 1020), then EIT process 1000 has collected enough measurement data and continues with a task 1026 (see FIG. 16). Task 1026 causes the EIT system to perform a reconstruction procedure, based upon the obtained current data and the voltage data. EIT process 1000 may leverage known reconstruction techniques, such as NOSER or FNOSER applications, to obtain electrical characteristics of the interior features of the body under test (task 1028). Such reconstruction methodologies are described in "Electrical Impedance Tomography," IEEE Signal Processing Magazine, November 2001, which is incorporated by reference herein. In particular, the reconstruction procedure processes the current and voltage data to determine/derive the respective impedances for the sections of the body under test (task 1030). In this regard, a "section" is located between a source electrode and a sink electrode, and the impedance for that section is derived from the current and voltage data obtained from the measurement using those designated source and sink electrodes. Eventually, EIT process 1000 can create an image of the interior features of the body under test (task 1032). Thus, the image is created in response to the measurement data and in response to the reconstruction procedure performed by the EIT system. The image may indicate different impedance/resistance values within the body as different colors, shades, or the like, where the variation in the image represents different types of structures within the body, e.g., bone, muscle, air, blood, etc.

While at least one example embodiment has been presented in the foregoing detailed description, it should be appreciated that a vast number of variations exist. It should also be appreciated that the example embodiment or embodiments described herein are not intended to limit the scope, applicability, or configuration of the invention in any way. Rather, the foregoing detailed description will provide those skilled in the art with a convenient road map for implementing the described embodiment or embodiments. It should be understood that various changes can be made in the function and arrangement of elements without departing from the scope of the invention as set forth in the appended claims and the legal equivalents thereof.

What is claimed is:

1. An electrical impedance tomography ("EIT") method for evaluating interior features of a region of a body under test with a plurality of electrodes, said method comprising:
    attaching a plurality of electrodes to the region of the body to form an electrode array surrounding the region, wherein each electrode of the plurality of electrodes comprises an electrode pad with at least one voltage lead and one current lead;
    designating a first one of the plurality of electrodes as a source electrode, and a second one of the plurality of electrodes as a sink electrode;
    establishing a virtual short between said source electrode and all other electrodes of the plurality of electrodes other than said sink electrode, wherein the virtual short is established by maintaining the source electrode and the all other electrodes at a predetermined voltage;
    applying a test current to said source electrode;
    measuring a sense voltage between said source electrode and said sink electrode; and
    repeating the designating, establishing, applying, and measuring steps for different source and sink electrodes in the plurality of electrodes; and
    reconstructing an image of the region of the body under test based on the applied test current and the measured sense voltage.

2. The EIT method according to claim 1, wherein the repeating of said designating, establishing, applying, and measuring steps is carried out for all possible combinations of source and sink electrodes.

3. The EIT method according to claim 1, wherein reconstructing the image of the region of the body under test based on the applied test current and the measured sense voltage comprises:

obtaining current data indicative of said test current;

obtaining voltage data indicative of said sense voltage, wherein the sense voltage corresponds to the test current; and performing a reconstruction procedure, based upon said current data and said voltage data, to obtain electrical characteristics of the interior features of the body under test.

4. The EIT method according to claim 3, image wherein obtaining the electrical characteristics of the of the interior features of the region of the body under test comprises calculating the impedance values from the stored current data and the stored voltage data.

5. The EIT method according to claim 3, wherein said reconstruction procedure determines an impedance for a section of the body under test, said section being located between said source electrode and said sink electrode.

6. An electrical impedance tomography ("EIT") method for evaluating interior features of a region of a body under test, said method comprising:

attaching a plurality of electrodes to form an electrode array surrounding the region of the body under test, wherein each electrode of the plurality of electrodes comprises an electrode pad with at least one voltage lead and one current lead;

controlling a switching network to designate, from said plurality of electrodes, a source electrode and a sink electrode;

maintaining all of said plurality of electrodes, other than said sink electrode, at an identical voltage to establish a virtual short between the source electrode and all other electrodes of the plurality of electrodes except the sink electrode;

applying a test current to said source electrode;

measuring a sense voltage between said source electrode and said sink electrode; and repeating the controlling, maintaining, applying, and measuring steps for different source and sink electrodes in the plurality of electrodes; and reconstructing an image of the region of the body under test based on the applied test current and the measured sense voltage.

7. The EIT method according to claim 6, wherein the repeating of said controlling, maintaining, applying, and measuring steps is carried out for all possible combinations of source and sink electrodes.

8. The EIT method according to claim 6, wherein reconstructing the image of the region of the body under test based on the applied test current and the measured sense voltage comprises:

storing current data indicative of said test current;

storing voltage data indicative of said sense voltage, wherein the sense voltage corresponds to the test current; and performing a reconstruction procedure, based upon said current data and said voltage data, to obtain electrical characteristics of the interior features of the region of the body under test.

9. The EIT method according to claim 8, image wherein obtaining the electrical characteristics of the of the interior features of the region of the body under test comprises calculating the impedance values from the stored current data and the stored voltage data.

10. The EIT method according to claim 8, wherein said reconstruction procedure determines an impedance for a section of the body under test, said section being located between said source electrode and said sink electrode.

11. An electrical impedance tomography ("EIT") system for evaluating interior features of a body under test, said EIT system comprising:

a plurality of electrodes configured to be attached to the body under test, each electrode comprises an electrode pad having a voltage lead and a current lead, wherein each electrode pad is configured to be attached to the body;

a switching network coupled to said plurality of electrodes, said switching network being configured to designate a first one of said plurality of electrodes as a source electrode, to designate a second one of said plurality of electrodes as a sink electrode, and to establish a virtual short between said source electrode and all other electrodes of said plurality of electrodes other than said sink electrode, wherein the virtual short is established by maintaining the source electrode and the all other electrodes at a predetermined voltage;

a current source coupled to said plurality of electrodes, said current source being configured to apply a test current to said source electrode, said test current producing a sense voltage between said source electrode and said sink electrode;

a voltage measurement element coupled to the switching network, wherein the voltage measurement element is configured to measure the sense voltage between the source electrode and the sink electrode;

an EIT processing unit coupled to said switching network, said EIT processing unit being configured to process test currents and corresponding sense voltage measurements generated in response to test currents; and wherein the switching network controls the current source and the voltage measurement element to repeat the designating, maintaining, applying, and measuring steps for different source and sink electrodes in the plurality of electrodes; and a display unit for displaying an image of the body under test, the image being created based on the applied test current and the measured sense voltage.

12. The EIT system according to claim 11, wherein said EIT processing unit, in creating the image based on the applied test current and the measured sense voltage, is configured to:

obtain current data indicative of said test current;

obtain voltage data indicative of said sense voltage, wherein the sense voltage corresponds to the test current; and perform a reconstruction procedure, based upon said current data and said voltage data, to obtain electrical characteristics of the interior features of the body under test.

13. The EIT system according to claim 12, wherein said EIT processing unit, in performing the reconstruction procedure, is configured to determine an impedance for a section of the body under test, said section being located between said source electrode and said sink electrode.

14. The EIT system according to claim 12, wherein the EIT processing unit is configured to create, in response to the reconstruction procedure, an image of the interior features of the body under test.

* * * * *

UNITED STATES PATENT AND TRADEMARK OFFICE
CERTIFICATE OF CORRECTION

PATENT NO. : 7,660,617 B2
APPLICATION NO. : 11/271776
DATED : February 9, 2010
INVENTOR(S) : Grant E. Davis It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 972 days.

Signed and Sealed this

Thirtieth Day of November, 2010

David J. Kappos
*Director of the United States Patent and Trademark Office*